(12) United States Patent
Nunes Nogueira et al.

(10) Patent No.: US 11,899,003 B2
(45) Date of Patent: Feb. 13, 2024

(54) UNIVERSAL ELECTRONIC BUNG SYSTEM

(71) Applicant: Watgrid, S.A., Ilhavo (PT)

(72) Inventors: Rogério Nunes Nogueira, Gafanha da Boa Hora (PT); Lúcia Maria Botas Bilro, Gafanha da Encarnação (PT); Fábio Patricio Domingues Gonçalves, Pombal (PT); Pedro Miguel Estima da Costa, Aveiro (PT); Ricardo José Ventura de Sousa e Carvalho Pereira, Oporto (PT)

(73) Assignee: Watgrid, S.A.

( * ) Notice: Subject to any disclaimer, the term of this patent is extended or adjusted under 35 U.S.C. 154(b) by 454 days.

(21) Appl. No.: 16/686,547

(22) Filed: Nov. 18, 2019

(65) Prior Publication Data

US 2020/0158708 A1 May 21, 2020

Related U.S. Application Data

(60) Provisional application No. 62/769,645, filed on Nov. 20, 2018.

(51) Int. Cl.
| | | |
|---|---|---|
| *G01N 33/14* | (2006.01) | |
| *C12H 1/22* | (2006.01) | |
| *B65D 90/48* | (2006.01) | |
| *G01F 23/80* | (2022.01) | |

(52) U.S. Cl.
CPC ........... *G01N 33/146* (2013.01); *B65D 90/48* (2013.01); *C12H 1/22* (2013.01); *G01F 23/80* (2022.01)

(58) Field of Classification Search
CPC ........... G01F 23/80; C12H 1/22; B65D 90/48; G01N 33/146

USPC .......................................................... 73/431
See application file for complete search history.

(56) References Cited

U.S. PATENT DOCUMENTS

| | | | |
|---|---|---|---|
| 4,368,639 A | 1/1983 | Owens | |
| 4,984,451 A | 1/1991 | Wilen | |
| 5,546,804 A * | 8/1996 | Johnson | G01D 11/245 73/431 |

(Continued)

FOREIGN PATENT DOCUMENTS

| | | |
|---|---|---|
| CN | 204214506 | 3/2015 |
| EP | 1270716 | 1/2003 |

(Continued)

OTHER PUBLICATIONS

Int'l Preliminary Report on Patentability Appln No. PCT/IB2019/001251 dated Jun. 3, 2021.

(Continued)

*Primary Examiner* — Nathaniel J Kolb
(74) *Attorney, Agent, or Firm* — McAndrews, Held & Malloy, Ltd.

(57) ABSTRACT

A method and system for monitoring wine in a barrel having a bung hole is provided. The system comprises a sensor enclosure, a sensor conduit, and an original bung. The sensor conduit is operably coupled to the sensor enclosure. The original bung comprises a passage hole for inserting the sensor conduit through the original bung. The original bung also comprises a space for inserting at least a portion of the sensor enclosure. This space does not extend through the original bung. The outer diameter of the original bung is determined by the diameter of the bung hole of the barrel.

20 Claims, 8 Drawing Sheets

(56) References Cited

U.S. PATENT DOCUMENTS

| | | | |
|---|---|---|---|
| 5,953,954 A | 9/1999 | Drain | |
| 7,659,980 B1 * | 2/2010 | Mitchell | G01N 21/53 356/338 |
| 2004/0076946 A1 | 4/2004 | Trauner et al. | |
| 2014/0081580 A1 * | 3/2014 | Kim | G01N 33/0004 702/24 |
| 2015/0198474 A1 | 7/2015 | Howard | |
| 2018/0136020 A1 * | 5/2018 | Sweet | H04L 67/10 |

FOREIGN PATENT DOCUMENTS

| | | | | |
|---|---|---|---|---|
| EP | 1462776 A1 * | 9/2004 | | G01F 23/74 |
| EP | 1462776 A1 | 9/2004 | | |
| GB | 2259974 A * | 3/1993 | | B22D 1/005 |
| WO | 2013028144 A3 | 2/2013 | | |
| WO | 2017216746 | 12/2017 | | |

OTHER PUBLICATIONS

Int'l Search Report and Written Opinion Appln No. PCT/IB2019/001251 dated Apr. 8, 2020.

Int'l Search Report and Written Opinion Appln No. PCT/IB2017/053549 dated Oct. 5, 2017 (6 pgs).

N. Oliveiram et al., Winegrid®: the remote and real-time wine production process monitoring system (6 pgs).

Portuguese Search Report Appln No. 109451 dated Nov. 18, 2016 (2 pgs).

Australian Examination Report No. 1 Appln No. 2019382977 dated May 5, 2022.

Australian Examination Report No. 2 Appln No. 2019382977 dated Jan. 10, 2023.

Australian Examination Report No. 3 Appln No. 2019382977 dated Apr. 19, 2023.

About—Sapere Liquid Knowledge [retrieved from internet on Apr. 18, 2023] < URL: https://web.archive.org/web/20180827112553/http:/sapereliquidknowledge.com/index.php/about-us/ Published on Aug. 27, 2018 as per Wayback Machine.

Di Gennaro, S. F., et al. 'Wireless real-time monitoring of malolactic fermentation in wine barrels: the Wireless Sensor Bung system', Australian Journal of Grape and Wine Research, Dec. 21, 2012, vol. 19, Issue 1, pp. 20-24.

Di Gennaro, S. F., et al., 'An Open-Source and Low-Cost Monitoring System for Precision Enology', Sensors, Dec. 5, 2014, vol. 14, Issue 12, pp. 23388-23397.

\* cited by examiner

Fig. 5A
Bung 307
Top View

Fig. 5B
Bung 307
Side View

Fig. 5C
Bung 307
Bottom View

UNIVERSAL ELECTRONIC BUNG SYSTEM

PRIORITY CLAIM

This patent application claims the benefit of priority to U.S. provisional patent application 62/769,645, titled "Universal Electronic Bung System," filed on Nov. 20, 2018. The above referenced document is hereby incorporated herein by reference in its entirety.

BACKGROUND

Limitations and disadvantages of conventional and traditional monitoring systems for winemaking will become apparent to one of skill in the art, through comparison of such systems with some aspects of the present invention as set forth in the remainder of the present application with reference to the drawings.

BRIEF SUMMARY OF THE INVENTION

Monitoring systems for winemaking substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

This disclosure describes systems for monitoring winemaking or other similar processes, for example. Many facets of wine change during the processes of maceration, fermentation and maturation. Parameters (e.g., pressure, temperature, density, distance, level, turbidity, color, pH, alcohol content) may be automatically captured continuously, periodically or otherwise over time and wirelessly transferred to a database for analysis and storage. Thresholds may be set such that a winemaker can be notified when the monitored parameters are out of a selected or desired range.

Figure 1:
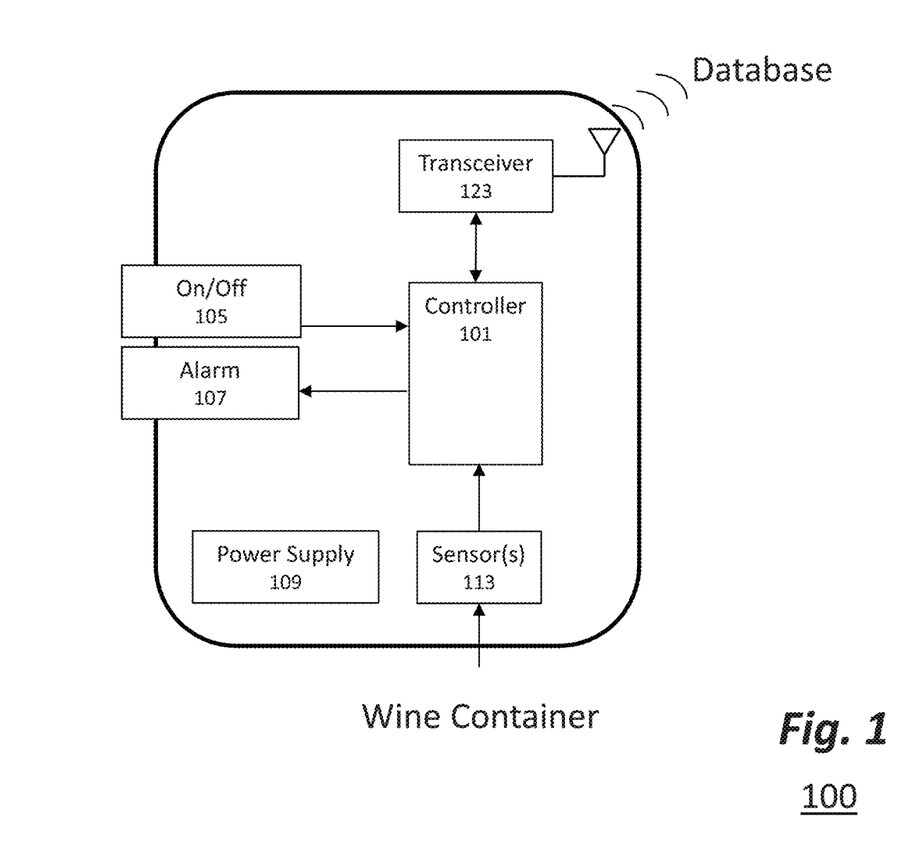
FIG. 1 illustrates components of a sensor device in accordance with an example implementation of this disclosure.

FIG. 1 illustrates components of a sensor device 100 in accordance with an example implementation of this disclosure. The depicted components of the sensor device 100 include a controller 101, an on/off switch 105, an alarm 107, a power supply 109, one or more sensor(s) 113, and a transceiver 123.

In operation, in a winemaking example, the sensor device 100 is coupled to a wine barrel or vat during a winemaking process. The one or more sensor(s) 113 may measure the temperature of the wine, and the one or more sensor(s) 113 measure additional parameters (e.g., pressure, density, distance, level, turbidity, color, pH, alcohol content) of the wine. These measurements are conveyed to the controller 101, which is operable to control a wireless transmission of the information, via transceiver 123, to a database for analysis and storage. Analysis of this information in the database may be performed by a remote device on the network. The transceiver 123 may use Bluetooth, WiFi, LoRa and/or any digital cellular standard. The sensor communicates with our computational platform built in a cloud based virtual machine.

The controller 101 may be operable to derive certain parameters from those supplied by the one or more sensor(s) 113. For example, a wine level may be derived according to a pressure or distance measurement. If the power supply 109 comprises one or more batteries, for example, the microcontroller 101 may be operable to monitor and report to the database when the batteries should be replaced or recharged.

The on/off switch 105 may comprise a button. Pressing the button 105 ON can trigger the sensor device 100 to send a beacon to enable pairing with a network. Pressing the button 105 OFF can trigger the sensor device 100 to store all current information in a Flash card before powering down. Button 105 may also be a non-touch capacitive button.

The sensor device 100 may generate local alarms. The alarm 107 may convey a visual and/or an audio alarm 107. Different sounds and/or different colors may indicate various conditions. A flashing red light or a beeping may indicate a low battery. A solid yellow light may indicate a low wine level and a need for topping off the wine. A solid blue light may indicate that the wine is below a low temperature threshold. The alarm 107 may comprise an LED. Such an LED may be incorporated into an on/off button 105. The alarm 107 may also be used to indicate the status of a pairing of the sensor device 100 to a local network.

The one or more sensor(s) 113 are operably coupled to a wine container, such as a barrel or a vat. The type of sensors used may depend of the current stage of winemaking. During maturation, for example, a pressure sensor may be used to measure a change in wine level. A distance sensor, based on time-of-flight measurements may also be used.

Figure 2:
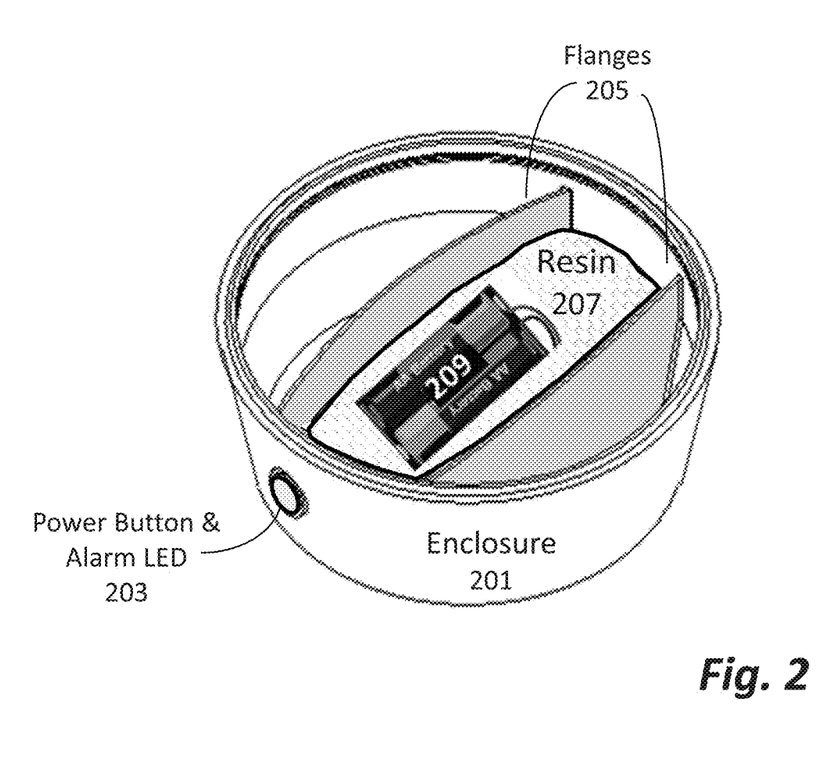
FIG. 2 illustrates an enclosure for a sensor device in a sensor system in accordance with an example implementation of this disclosure.

FIG. 2 illustrates an enclosure 201 for a sensor device 100 (as described regarding FIG. 1) in a sensor system in accordance with an example implementation of this disclosure. The enclosure comprises an LED incorporated into an on/off button 203 to provide an alarm as well as power control. The electronic circuitry (i.e., controller 101, sensor(s) 113 and transceiver 123 as described regarding FIG. 1) and an antenna may be mounted in the enclosure 201 and encased in resin 207 for durability and to protect from moisture. The resin area 207 may also be limited by flanges 205. Batteries 209 are accessible above the resin 207 to enable replacement by a user. The batteries may be, for example, AA, AAA or and other size.

Figure 3A:
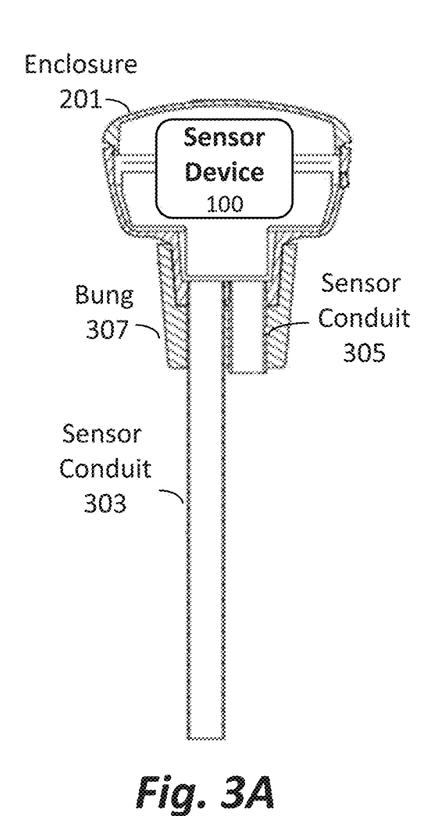
FIG. 3A illustrates a cut-away view of a sensor system comprising a sensor device and a removable bung in accordance with an example implementation of this disclosure.

FIG. 3A illustrates a cut-away view of a sensor system comprising a sensor device 100 in accordance with an example implementation of this disclosure. The depicted components of the sensor system include the sensor device 100 in an enclosure 201, one or more sensor conduits 303 and/or 305, and a replaceable bung 307. In a sensor system with one sensor conduit 303, for example, sensor conduit 305 would not exist. The enclosure 201 may be made of flexible plastic or hard rubber. The sensor conduits 303 and 305 may be stainless steel. The bung 307 may be made of silicone.

Figure 3B:
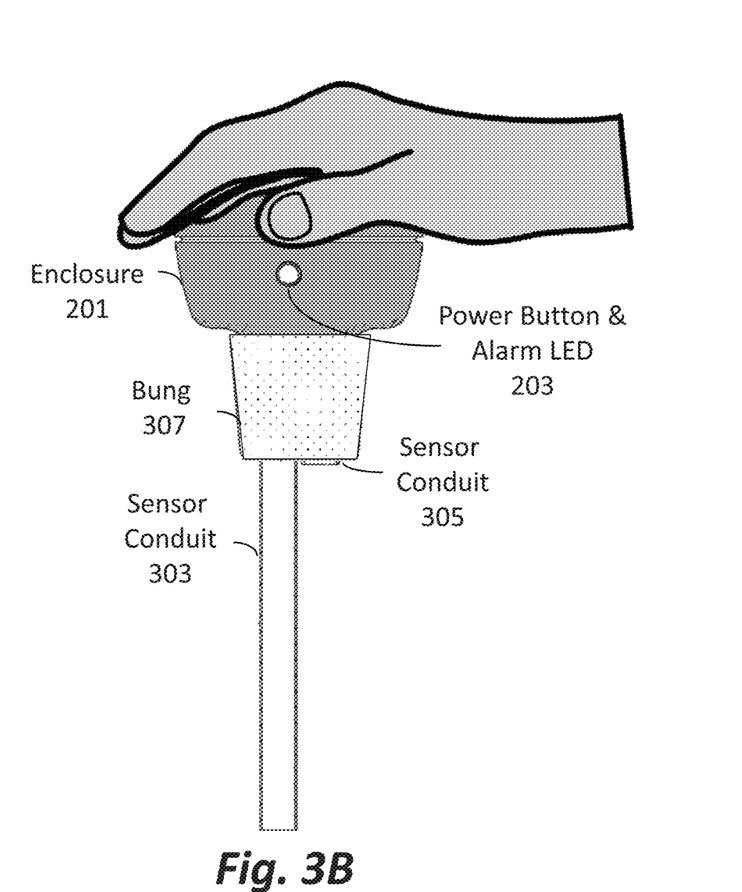
FIG. 3B illustrates a sensor system comprising a sensor device and a removable bung in accordance with an example implementation of this disclosure.

FIG. 3B illustrates an external view of the same sensor system as shown FIG. 3A. The enclosure 201 is ergonomically designed to fit a human hand to aid installation and removal. Accordingly, an example diameter of the enclosure 201 is 3½ to 4½ inches (90 to 115 mm).

The bung 307 can be interchanged without affecting the rest of the sensor system. For example, the bung 307 may deteriorate over time. Replacement of a silicone bung 307 is more cost effective than replacing the entire sensor system. Also, different barrels may have different sized bung holes. Replacing the silicone bung 307 allows a winemaker to use the same monitor regardless of the barrel or the size of the bung hole.

Figure 4A:
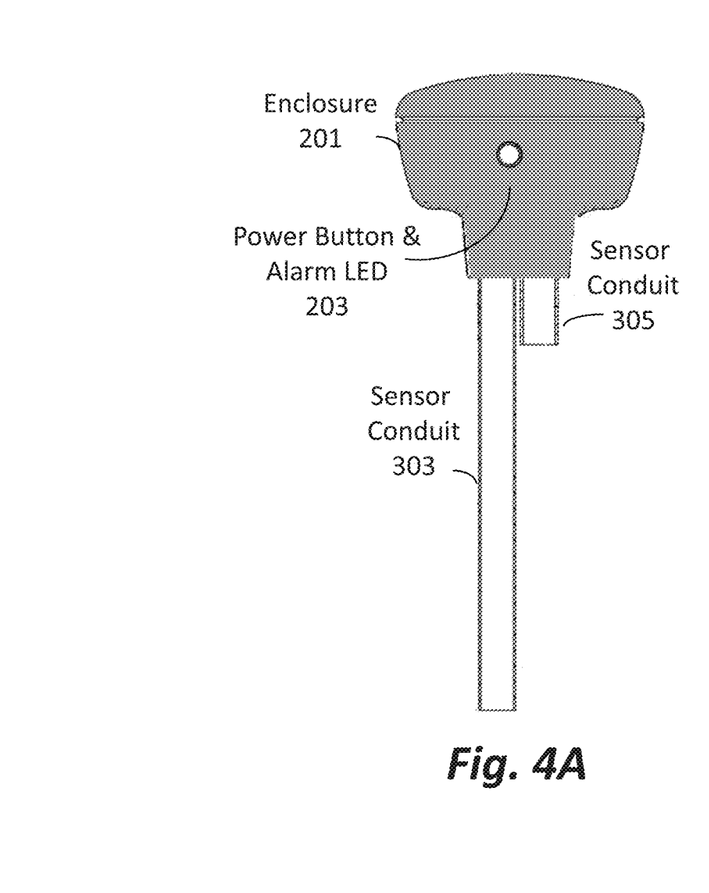
FIG. 4A illustrates a sensor system comprising a sensor device in accordance with an example implementation of this disclosure.
Figure 4B:
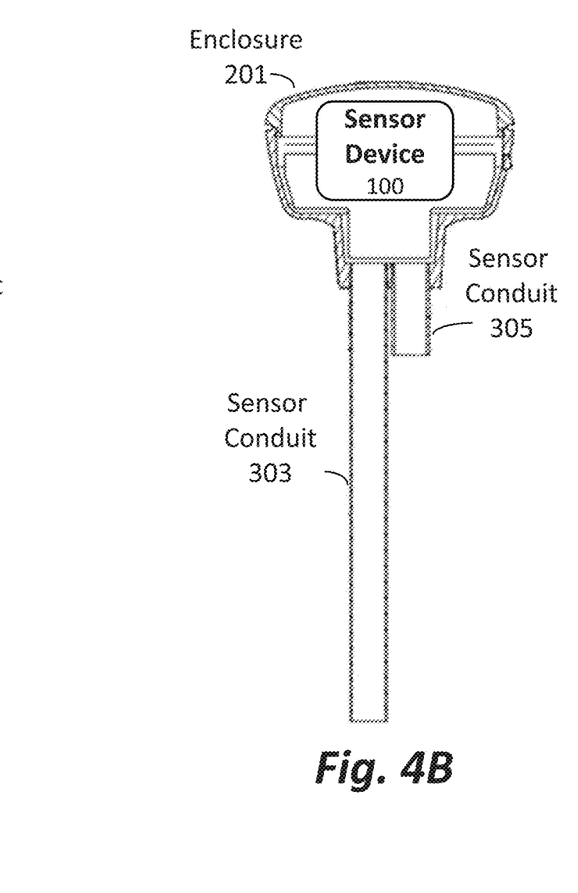
FIG. 4B illustrates a cut-away view of a sensor system comprising a sensor device in accordance with an example implementation of this disclosure.

FIG. 4A illustrates an external view of the same sensor system as shown FIGS. 3A and 3B when the bung 307 is removed. FIG. 4B illustrates a cut-away view of the same sensor system as shown FIG. 4A.

Figure 5A:
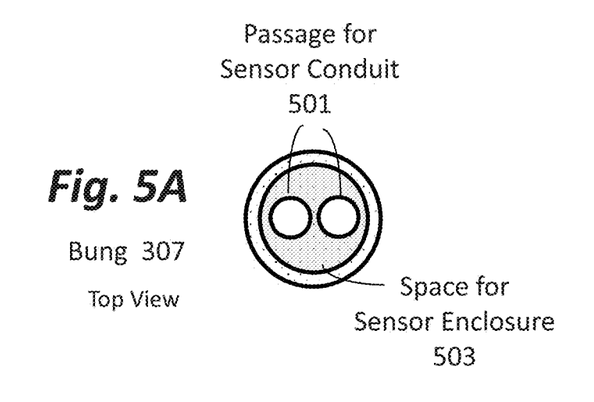
FIG. 5A illustrates a top view of a removable bung in accordance with an example implementation of this disclosure.
Figures 5B, 5C:
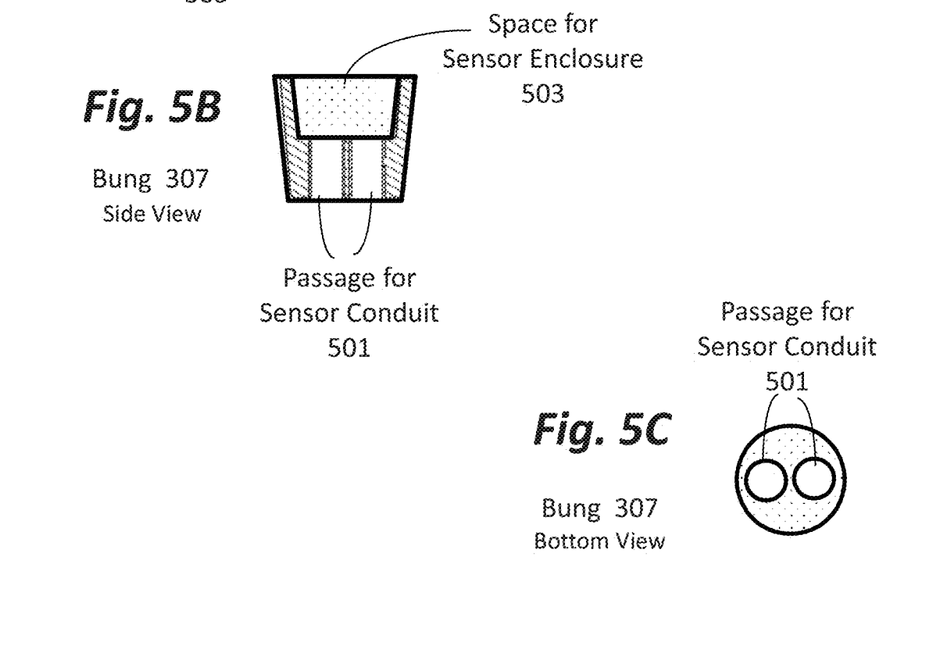
FIG. 5B illustrates a cut-away side view of a removable bung in accordance with an example implementation of this disclosure.
FIG. 5C illustrates a bottom view of a removable bung in accordance with an example implementation of this disclosure.

FIG. 5A illustrates a top view of the removable bung 307. FIG. 5B illustrates a cut-away side view of the removable bung 307. FIG. 5C illustrates a bottom view of the removable bung 307. A sensor system may comprise one or more sensor conduits 303 and 305. Accordingly, the bung 307 has a passage hole for each of the one or more sensor conduits 303 and 305. Additionally, the bung 307 may fit around the sensor enclosure 201. A space 503 for the sensor enclosure 201 is provided from the top of the bung 307.

Figure 6A:
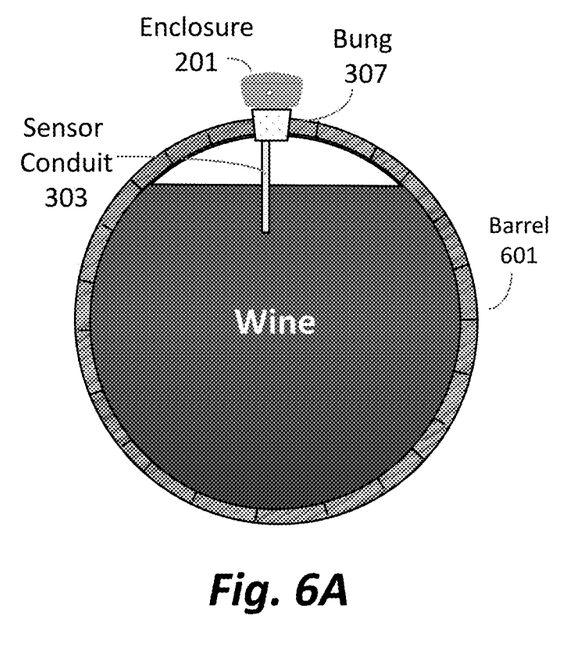
FIG. 6A illustrates a cut-away side view of a sensor system in a wine barrel in accordance with an example implementation of this disclosure.

FIG. 6A illustrates a cut-away side view of a sensor system in a wine barrel 601. The sensor system is inserted into the barrel 601 and held in place by the bung 307. One or more sensor conduits 303 and 305 are in contact with the wine. One or more sensor conduits 303 and 305 within the bung 307 are in contact with the space above the wine. Only the sensor device enclosure 201 and partially the bung 307 are visible from the outside of the wine barrel 601.

Figure 6B:
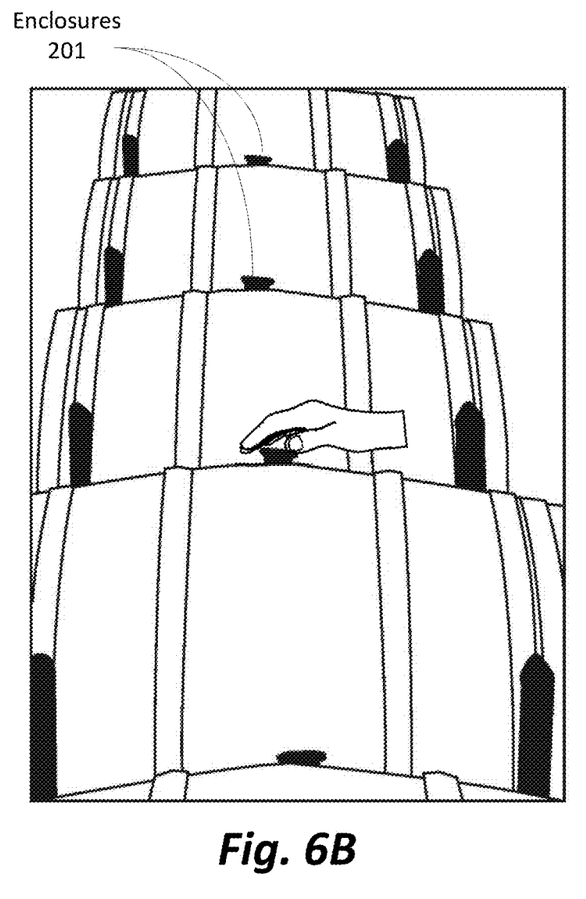
FIG. 6B illustrates a top view of sensor systems in wine barrels in accordance with an example implementation of this disclosure.

FIG. 6B illustrates a top view of a plurality of sensor systems in wine barrels.

Figure 7:
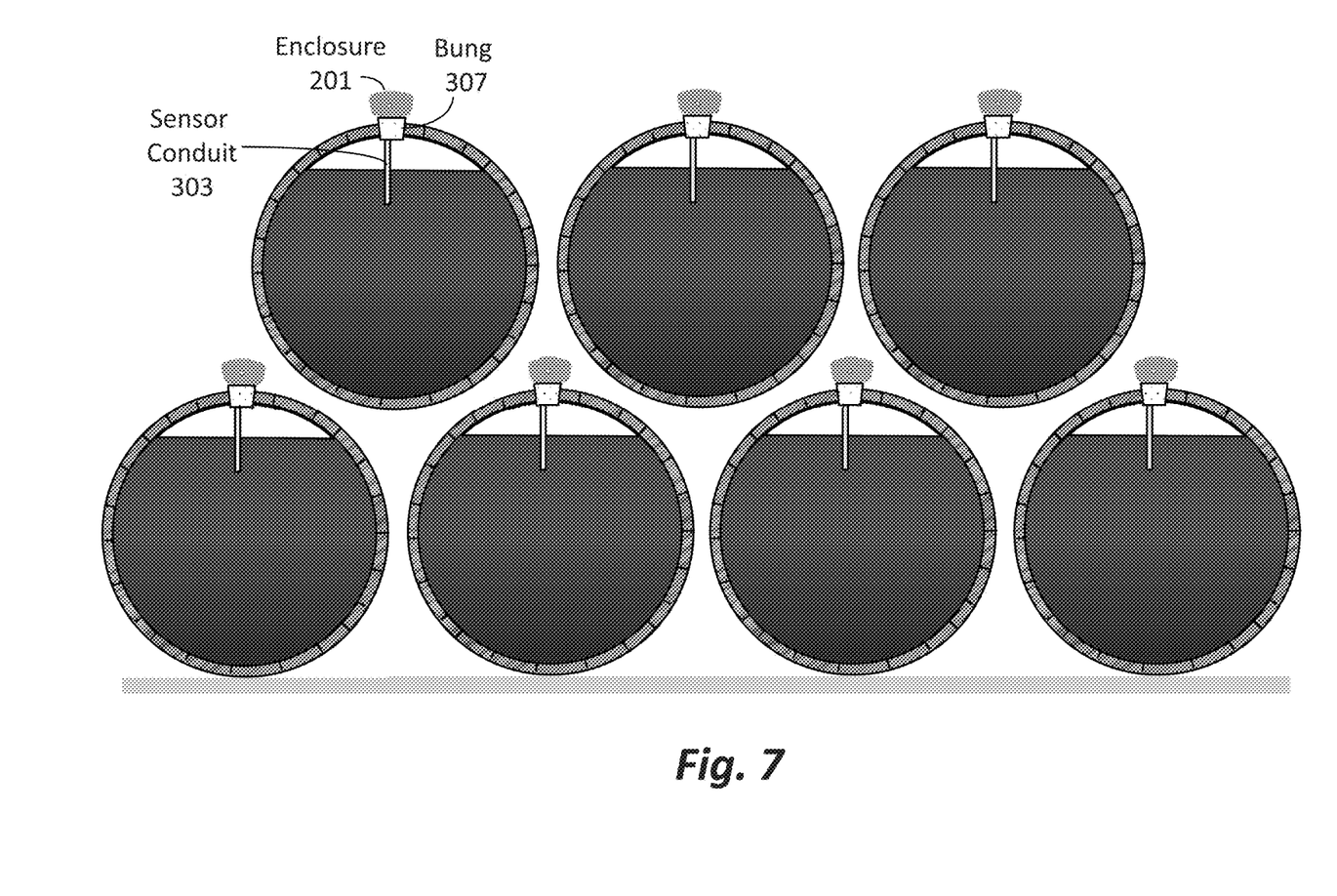
FIG. 7 illustrates a cut-away side view of sensor systems in stacked wine barrels in accordance with an example implementation of this disclosure.

FIG. 7 illustrates a cut-away side view of the sensor systems in stacked wine barrels. A sensor system is inserted into each barrel and held in place by the bung 307. One or more sensor conduits 303 and 305 are in contact with the wine in each barrel.

Figure 8:
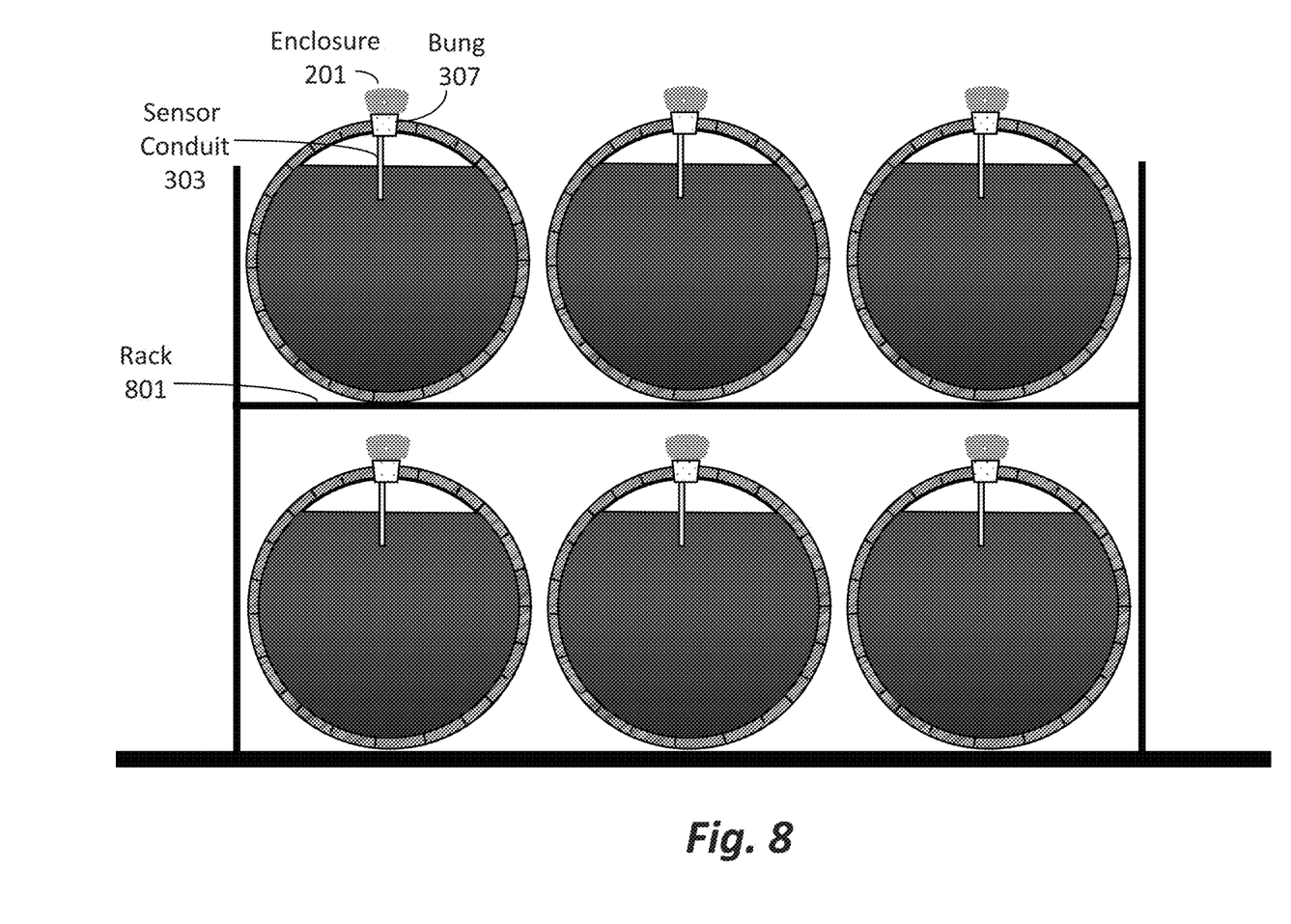
FIG. 8 illustrates a cut-away side view of sensor systems in racked wine barrels in accordance with an example implementation of this disclosure.

FIG. 8 illustrates a cut-away side view of sensor systems in racked wine barrels. A sensor system is inserted into each barrel and held in place by the bung 307. One or more sensor conduits 303 are in contact with the wine in each barrel. The sensor device enclosure 201 is short enough to fit under the rack 801.

The enclosure 201 is designed to allow wine barrels to be stacked as illustrated in FIG. 7 or racked as illustrated in FIG. 8. Accordingly, an example height of the enclosure 201 is less than 2½ inches (64 mm).

A system (e.g., FIGS. 3A, 3B, 4A and 4B) for monitoring wine in a barrel having a bung hole is provided. The system comprises a sensor enclosure (e.g., 201), one or more sensor conduits (e.g., 303, 305), and an original bung (e.g., 307). One or more sensor conduits (e.g., 303, 305) are operably coupled to the sensor enclosure (e.g., 201). The sensor conduits (e.g., 303, 305) may also be detached from the sensor enclosure (e.g., 201) temporarily for cleaning procedures. The original bung (e.g., FIGS. 5A, 5B and 5C) comprises one or more passage holes (e.g., 501) for inserting the sensor conduit (e.g., 303, 305) through the original bung (e.g., 307). In a sensor system with one sensor conduit 303, for example, the passage for the sensor conduit 501 would only have one hole. The original bung (e.g., 307) also comprises a space (e.g., 503) for inserting at least a portion of the sensor enclosure (e.g., 201). This space (e.g., 503) does not extend through the original bung. The outer diameter of the original bung is determined by the diameter of the bung hole of the barrel.

The original bung may be interchanged with an alternative bung that has an outer diameter that may or may not be a different size. Such interchangeability allows the winemaker to use barrels with different bung hole sizes, while not requiring the extra time and expense of a new sensor conduit (e.g., 303, 305) and new enclosure (e.g., 201) with new sensor electronics. Such interchangeability also allows the winemaker to reuse the sensor conduit (e.g., 303, 305) and the enclosure (e.g., 201) even after the original bung has worn out.

As shown in FIG. 1, the sensor enclosure (e.g., 201) may comprise a power supply (e.g., 109) and a controller (e.g., 101). The controller (e.g., 101) is also able to wirelessly communicate with a remote database via the transceiver (e.g., 123).

The controller (e.g., 101) may be encased in a resin (e.g., 207 of FIG. 2), while the power supply (e.g., 109) remains accessible above the resin (e.g., 207). Such encasement provides protection to the controller (e.g., 101) from, for example, water and misuse. The resin (e.g., 207) may fill a volume between two flanges (e.g., 205) within the sensor enclosure (e.g., 201). An antenna, operably coupled to the controller (e.g., 101) and transceiver (e.g., 123) is may be located on the surface of one of the two flanges (e.g., 205).

An outer dimension across the sensor enclosure (e.g., 201) may be 3½ to 4½ inches to allow the winemaker to grasp the sensor enclosure as illustrated in FIG. 3B. The height of the sensor enclosure may be less than 2½ inches to allow the wine barrels to be stacked as illustrated in FIG. 7 and/or racked as illustrated in FIG. 8.

The aforementioned system enables the winemaker to monitor the wine by inserting a sensor conduit (e.g., 303 and/or 305) through one or more passage holes (e.g., 501) in an original bung (e.g., 307); inserting the sensor enclosure (e.g., 201) into the original bung (e.g., 307); and inserting the original bung (e.g., 307) into the bung hole of the original barrel.

The winemaker can also swap bungs by removing the original bung (e.g., 307) from the bung hole of the barrel; removing the original bung (e.g., 307) from the sensor enclosure (e.g., 201) and the sensor conduit (e.g., 303 and/or 305); inserting the sensor conduit (e.g., 303 and/or 305) through a passage hole in an alternative bung; inserting the sensor enclosure (e.g., 201) into the alternative bung; and inserting the alternative bung into a bung hole of an alternative barrel.

As utilized herein the terms "circuits" and "circuitry" refer to physical electronic components (i.e. hardware) and any software and/or firmware ("code") which may configure the hardware, be executed by the hardware, and or otherwise be associated with the hardware. As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

The present invention may be realized in hardware, software, or a combination of hardware and software. The present invention may be realized in a centralized fashion in at least one computing system or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

The present invention may be realized in a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

While the present invention has been described with reference to certain embodiments, it will be understood by those skilled in the art that various changes may be made and equivalents may be substituted without departing from the scope of the present invention. Those skilled in the art will understand that, in addition to winemaking, the present invention may be used for making of other products (e.g., whiskey, cognac, brandy, rum, gin, vodka, tequila, beer) without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A system for monitoring wine in a barrel having a bung hole,
wherein the system comprises:
a sensor enclosure;
a sensor device within the sensor enclosure;
a sensor conduit operably coupled to the sensor enclosure; and
an original bung, wherein:
the original bung is a conical frustum that comprises a passage hole for inserting the sensor conduit through the original bung,
the original bung comprises a space for inserting at least a portion of the sensor enclosure,
the space does not extend through the original bung,
an outer diameter of the original bung is determined by a diameter of the bung hole of the barrel,
the sensor device is not configured for monitoring the sensor enclosure, and
the original bung is configured to be separable from the sensor device and the sensor enclosure without requiring a removal of more than the conical frustum.

2. The system according to claim 1, wherein:
the system comprises an alternative bung,
the original bung is interchangeable with an alternative bung, and
an outer diameter of the alternative bung is different than the outer diameter of the original bung.

3. The system according to claim 1, wherein:
the system comprises an alternative bung,
the original bung is interchangeable with a replacement bung, and
an outer diameter of the replacement bung is the same as the outer diameter of the original bung.

4. The system according to claim 1, wherein the sensor enclosure comprises a power supply and a controller, and wherein the controller is operable to wireless communicate with a remote database.

5. The system according to claim 4, wherein the controller is encased in a resin, and wherein the power supply accessible above the resin.

6. The system according to claim 5, wherein the resin fills a volume between two flanges within the sensor enclosure.

7. The system according to claim 6, wherein an antenna is located on the surface of one of the two flanges, and the antenna is operably coupled to the controller.

8. The system according to claim 1, wherein an outer dimension across the sensor enclosure is 3½ to 4½ inches.

9. The system according to claim 1, wherein a height of the sensor enclosure is less than 2½ inches.

10. The system according to claim 1, wherein the system comprises the barrel.

11. A method for monitoring wine in an original barrel having a bung hole, wherein the method comprises:
inserting a sensor conduit through a passage hole in an original bung, wherein the sensor conduit is operably coupled to a sensor enclosure comprising a sensor device;
inserting the sensor enclosure into the original bung, wherein:
the original bung is a conical frustum that comprises a space for inserting at least a portion of the sensor enclosure, the space does not extend through the original bung, the sensor device is not configured for monitoring the sensor enclosure, the original bung is configured to be separable from the sensor device and the sensor enclosure without requiring a removal of more than the conical frustum, and the original bung is interchangeable with an alternative bung;

inserting the original bung into the bung hole of the original barrel, wherein an outer diameter of the original bung is determined by a diameter of the bung hole of the original barrel; and using the sensor device to determine a parameter of the wine in the original barrel.

12. The method according to claim 11, wherein the method comprises:

removing the original bung from the bung hole of the barrel;

removing the original bung from the sensor enclosure and the sensor conduit;

inserting the sensor conduit through a passage hole in an alternative bung, wherein the sensor conduit is operably coupled to the sensor enclosure, and wherein an outer diameter of the alternative bung is different than the outer diameter of the original bung;

inserting the sensor enclosure into the alternative bung, wherein the alternative bung comprises a space for inserting at least a portion of the sensor enclosure, and wherein the space does not extend through the alternative bung; and inserting the alternative bung into a bung hole of an alternative barrel, wherein a diameter of the bung hole of the alternative barrel is different than the diameter of the bung hole of the original barrel.

13. The method according to claim 11, wherein the method comprises:

removing the original bung from the bung hole of the original barrel;

removing the original bung from the sensor enclosure and the sensor conduit;

inserting the sensor conduit through a passage hole in a replacement bung, wherein the sensor conduit is operably coupled to the sensor enclosure, and wherein an outer diameter of the replacement bung is the same as the outer diameter of the original bung;

inserting the sensor enclosure into the replacement bung, wherein the replacement bung comprises a space for inserting at least a portion of the sensor enclosure, and wherein the space does not extend through the replacement bung; and inserting the replacement bung into the bung hole of the original barrel.

14. The method according to claim 11, wherein the sensor enclosure comprises a power supply and a controller, and wherein the controller is operable to wireless communicate with a remote database.

15. The method according to claim 14, wherein the controller is encased in a resin, and wherein the power supply accessible above the resin.

16. The method according to claim 15, wherein the resin fills a volume between two flanges within the sensor enclosure.

17. The method according to claim 16, wherein an antenna is located on the surface of one of the two flanges, and the antenna is operably coupled to the controller.

18. The method according to claim 11, wherein an outer dimension across the sensor enclosure is 3½ to 4½ inches.

19. The method according to claim 11, wherein a height of the sensor enclosure is less than 2½ inches.

20. The method according to claim 11, wherein the barrel is one of a plurality of barrels in a rack, and wherein the method is repeated for other barrels in the rack.

* * * * *